United States Patent [19]

Romanet et al.

[11] Patent Number: 5,688,964
[45] Date of Patent: Nov. 18, 1997

[54] PROCESS FOR PREPARING A ACYLHYRAZINO PYRAZOLE DERIVATIVE

[75] Inventors: Robert Fogg Romanet; Susan Marie Fischer, both of Rochester, N.Y.

[73] Assignee: Eastman Kodak Company, Rochester, N.Y.

[21] Appl. No.: 600,714

[22] Filed: Feb. 13, 1996

[51] Int. Cl.[6] .................................................. C07D 231/38
[52] U.S. Cl. ................................. 548/371.7; 548/262.4
[58] Field of Search ........................................ 548/371.7

[56] References Cited

U.S. PATENT DOCUMENTS 4,477,448  10/1984  Hamberger et al. ................. 548/371.1

OTHER PUBLICATIONS

J. Prakt. Chem. 323, (6) 965, 1981.

Primary Examiner—Robert W. Ramsuer
Attorney, Agent, or Firm—Arthur E. Kluegel

[57] ABSTRACT

A process for making a compound of formula III

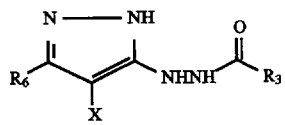

wherein
  $R_6$ is a group bonded to the rest of the molecule by a carbon atom;
  $R_3$ is a group containing a carbon atom and bonded to the rest of the molecule by a carbon atom or by a heteroatom; and
  X is hydrogen or a substituent, comprising:
  reacting with hydrazine a compound of formula II

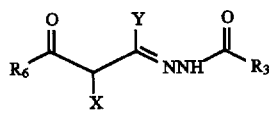

or a dehydrated analog of formula II, wherein $R_3$, $R_6$, and X have the same meaning as for formula III, and Y is a nucleofugal leaving group.

9 Claims, No Drawings

PROCESS FOR PREPARING A ACYLHYRAZINO PYRAZOLE DERIVATIVE

FIELD OF THE INVENTION

The invention relates to a acylhydrazino pyrazole derivative, a process for preparing the derivative, and a process for preparing a pyrazolo[5,1-c]-1,2,4-triazole coupler compound therefrom which coupler is useful as a dye forming coupler in photographic imaging.

BACKGROUND OF THE INVENTION

Numerous pyrazole derivatives are known in the art. Many of these derivatives are of value as intermediate compounds in multi-step processes for the manufacture of a more complex pyrazole derivative compound. Such complex compounds are useful, for example, in the pharmaceutical, photographic or dye industries. The known intermediates and processes for preparing such intermediates have not been altogether satisfactory. They have not provided flexibility in the ability to prepare the desired end product that is required and have often relied on raw materials that are not readily available or on complicated process steps.

The acylhydrazino pyrazole derivative of the invention is readily prepared and is useful as an intermediate for preparing dye-forming couplers derived from pyrazolo[5,1-c]-1,2,4-triazole compounds. These couplers may provide cyan or magenta dyes and magenta dyes formed from the couplers generally have a hue advantage over commonly used magenta dye-forming couplers derived from 5-pyrazolones (J. Chem. Soc. Perkin 1, 2047, 1977).

The manufacture of the complicated bicyclic pyrazolo[5,1-c]-1,2,4-triazole compounds is expensive, partly due to the many steps necessary to form the chromophore and partly due to the need to deal with the toxicity and thermal instability of some of the intermediates. In some preparations sulfur is formed as a by-product and affects adversely the photographic properties if not removed completely. Overall yields are often quite low.

It is known to prepare pyrazolo[5,1-c]-1,2,4-triazoles from 1,2,4-triazolo[3,4-b][1,3,4]thiadiazines by ring contraction and sulfur elimination. Yields are not high and the sulfur by-product is difficult to remove. See, for example, the above cited J. Chem. Soc. article, Chem. Ber. 89 2550 (1956), Research Disclosure 12443 (1974), and EP 285274 (1988). Thiocarbohydrazide or carbon disulfide is used as the starting material for the 1,2,4-triazolo[3,4-b][1,3,4] thiadiazines (EP 347235, EP 284240, JP 61-260085) which require special handling during manufacture due to their hazardous nature. It is also known to condense 3,4-diamino-1,2,4-triazoles with beta-ketoesters to form an isomeric mixture of 1,2,4-triazolo[4,3-b]-1,2,4-triazepine-6-one and 1,2,4-triazolo[4,3-b]-1,2,4-triazepine-8-one, of which only the former can be converted to the desired pyrazolo[5,1-c]-1,2,4-triazole (Arch. Phar. 303, 709 (1970) and J. Heterocycl. Chem. 11, 751 (1974)). The target couplers can also be prepared by photolysis of 7-diazo-1,2,4-triazolo[4,3-b] pyridazine-8-ones (J. Prakt. Chem. 314, 55, (1972); J. Heterocycl. Chem. 16, 195 (1975)) but photolysis on an industrial scale is not practical. Decarboxylation under harsh conditions of heat in the presence of acids or bases is required for some other syntheses (EP 182617, EP 178789, EP 287265, DD 263060, EP 217353, EP 269436, JP 01-233285) and these conditions, aside from contributing to high costs, are not compatible with other functionalities in the molecule. Pyrazolo[5,1-c]-1,2,4-triazole compounds can also be made from 3(5)-aminopyrazoles by diazotization and coupling with compounds having an acidic —CH— group followed by ring closure (J. Heterocycl. Chem. 14 227 (1977), Arch. Pharm. Res. 10, 14 (1987), Monatsh. Chem. 112 245 (1981), JP 02 115183). These methods suffer the drawback that they only result in a limited number of possible akyl substituents in the 3-position of the coupler. This same starting material can also be made to react with a hydroximoyl chloride followed by reaction with a sulfonyl chloride, acetylation, ring closure, and deacetylation ((DE 4,211,479) but the number of steps is rather cumbersome and the yields variable. The same starting material can also be diazotized and then reduced to yield an 3(5)-hydrazinopyrazole (DE 3708333, JP 61-249969, JP 62-158259) which can be then reacted with an aldehyde and cyclized to a pyrazolotriazole or reacted with an acid chloride (an easier route to such a compound is found in J. Prakt. Chem. 323, (6) 965, (1981) but doesn't lead to a useful pyrazolotriazole when cyclized due to the presence of an amine substituent in the 3-position) and cyclized. This route suffers from low yields, difficult isolation, and waste disposal problems during the reduction step (Anales de Quimica 66, 911 (1970)). Other examples in the art can be found in JP 63/150284, DD 263,060, U.S. Pat. No. 4,791,052 and U.S. Pat. No. 4,777,121.

A problem to be solved is to provide a process for preparing a acylhydrazino pyrazole derivative intermediate and a process for transforming the intermediate into a pyrazolo[5,1-c]-1,2,4-triazole compound which advantageously provides a simplified process for the preparation of the intermediate and the coupler compound from readily available starting materials.

SUMMARY OF THE INVENTION

The invention provides compound II and a process for making a compound of formula III from compound II

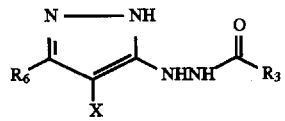   III wherein

R$_6$ is a group bonded to the rest of the molecule by a carbon atom;

R$_3$ is a group containing a carbon atom and bonded to the rest of the molecule by a carbon atom or by a heteroatom; and X is hydrogen or a substituent, comprising:

reacting with hydrazine a compound of formula II

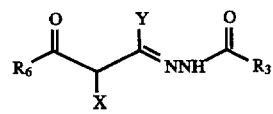   II or a dehydrated analog of formula II, wherein R$_3$, R$_6$, and X have the same meaning as for formula III, and Y is a nucleofugal leaving group.

The invention also provides a process for transforming the compound II into a dye forming coupler.

The processes of the invention are simple and rely on readily available materials.

DETAILED DESCRIPTION OF THE INVENTION

The invention is generally described in the Summary of the Invention. A general scheme for the synthesis of compound III may be summarized as follows:

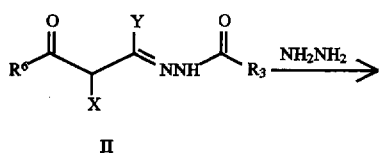

II

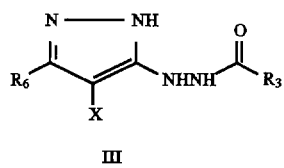

III $R_6$ may be any substituent group bonded to the rest of the molecule by a carbon atom. It may be chosen, for example, from alkyl, aryl, or heterocyclic groups, unsubstituted or substituted with substituents which will not undergo undesirable side reactions under the reaction conditions. $R_3$ may be chosen from the same groups as $R_6$ and may also be a substituent linked to the rest of the compound by a heteroatom such as nitrogen, sulfur, or oxygen. To minimize the number of steps in preparing a useful coupler compound having a carbon-linked substituent as $R_3$, $R_3$ may be the substituent ultimately desired in the end product. On the other hand, it may start out as a replaceable substituent which may have a heteroatom link to the acyl carbon.

$R_3$ and $R_6$ can be, for example, methyl, ethyl, propyl, butyl, octyl, hexadecyl, octadecyl, isopropyl, tertiary butyl, t-pentyl, t-octyl, adamantyl, 3-phenylpropyl, 4'-nitro-3-phenylpropyl, 3-chloropropyl, phenyl, naphthol, 2-pyridyl, 2-methoxyphenyl, 2-aminoalkyl, 3-alkylsulfonylpropyl, 3-phenoxypropyl, 1-methyl-2-sulfonamidoethyl, 1-methyl-2-acylaminoethyl, etc. They may thus be optionally substituted, for example, with halides, esters, ethers, sulfones, nitro, nitriles, sulfonamides, acylamines, amines, etc. Often, $R_6$ is linked to the rest of the molecule by a tertiary carbon or a phenyl group. When I is to be a photographic coupler, $R_3$ will typically contain or be converted to contain a ballast group of eight or more aliphatic carbon atoms designed to render the coupler nondiffusible during development. Groups that are reactive under the reaction conditions of this or subsequent reaction steps (which will not undergo undesirable modifications) may also be used. For example, during the dehydration step (discussed hereafter) an aliphatic alcohol will be converted to a chloride (see synthetic example); amides may be converted to nitriles; phenols may be converted to phosphates; acids to acid chlorides, etc.

Particularly suitable for $R_3$ and $R_6$ are straight chained or branched alkyl groups optionally substituted with ether, sulfone, amine, acylamine, or aryl groups which may be optionally substituted, for example, with alkyl, nitro, ester, halogen, or ether groups. Particularly convenient are unsubstituted straight chain or branch alkyl or aralkyl groups and those substituted with phenyl, methoxyphenyl, nitrophenyl, chloro, sulfone, ether, or ester groups.

X may be hydrogen or any substituent group. When it is desired to ultimately form a photographic coupler compound, then it is desirable that X is (1) hydrogen or (2) a group which is either (a) capable of being eliminated during reaction with oxidized developer as described hereinafter, or (b) a group capable of being eliminated or replaced by a group as described for (a) during a reaction subsequent to the reaction with oxidized developer. Representative classes of such groups capable of being eliminated or replaced include, for example, halogen, alkoxy, aryloxy, hetero-oxy, sulfonyloxy, acyloxy, acyl, heterocyclyl, sulfonamido, mercaptotetrazole, benzothiazole, mercapto-propionic acid, phosphonyloxy, arylthio, and arylazo. Coupling-off groups capable of being eliminated during reaction with oxidized developer are described in the art, for example, in U.S. Pat. Nos. 2,455,169, 3,227,551, 3,432,521, 3,476,563, 3,617,291, 3,880,661, 4,052,212 and 4,134,766; and in UK. Patents and published application Nos. 1,466,728, 1,531,927, 1,533,039, 2,006,755A and 2,017,704A. Suitable such groups include chlorine and those bonded to the rest of compound I by a heteroatom such as oxygen, sulfur or nitrogen. Typical examples are halogen, alkoxy, aryloxy, sulfide, alkylthio, arylthio, heterocycle such as a nitrogen heterocycle, azo, or other commonly used photographically useful fragment known in the art. Particularly suitable are chloride and substituted or unsubstituted aryloxy. The same proviso with regard to surviving the reaction conditions mentioned above applies to the selection of X. It is noted that it is not necessary that the group X included in the compounds of the process of the invention must remain unchanged throughout the process. In fact, it is possible to add or substitute to obtain the desired X group before, in between or subsequent to the above process steps.

Y in this reaction is a nucleofugal leaving group. A leaving group that carries away an electron pair is called nucleofugal. (J.March, Advanced Organic Chemistry, John Wiley and Sons, New York, N.Y., 1985, p 179.) Suitable examples of Y groups are halide, alkoxide, phenoxide, carboxylate, phosphate, sulfide, sulfoxide, sulfone, sufonamide and the like. Particular examples are halide, alkoxide, phenoxide carboxylate, and sulfide. Halide and alkoxide are most conveniently used.

If used as part of a process to prepare a pyrazolo[5,1-c]-1,2,4-triazole, compound III is then reacted with a dehydrating agent to form compound I.

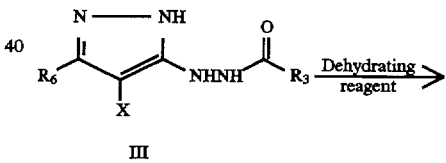

III

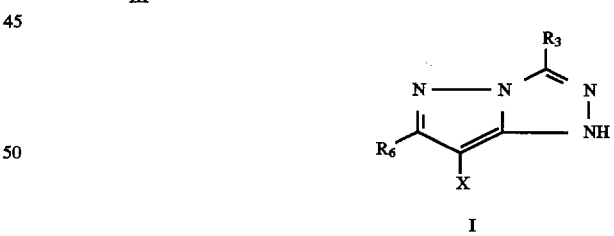

I

If desired, both steps of the process can be carried out in one vessel or the intermediate III may be isolated before the second step is performed. The first step is the reaction of the acylhydrazino pyrazole derivative II with hydrazine to form the substituted pyrazole III.

If desired, the following reaction between an imino ether IV and a hydrazide V may be conducted in an ethanol solvent to obtain the acylhydrazino pyrazole derivative starting material II:

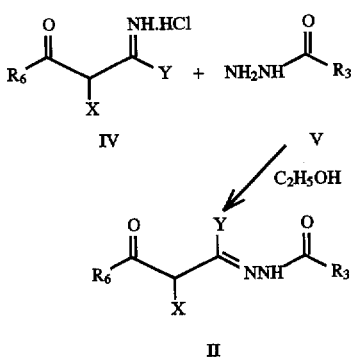

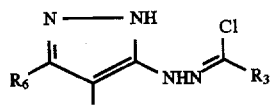

Any inert organic solvent may be employed to prepare II with the lower aliphatic alcohols such as ethanol or methanol being typically suitable. The reaction proceeds at room temperature in less than an hour using the batch sizes tested.

Compound II having the desired $R_3$ and $R_6$ groups is reacted with hydrazine to close the pyrazole ring and yield compound III. If compound II is made as described above, compound II may be isolated or not as desired before it is reacted with the hydrazine. Water or any inert organic solvent may be employed as the reaction medium. Suitable examples include lower alcohols, methylene chloride, chloroform, tetrahydrofuran, diethyl ether, ethyl acetate, acetic acid, pyridine, and acetonitrile. Methanol, ethanol or ethyl acetate are conveniently employed as the reaction medium. Temperatures ranging from −78° C. to the boiling point of the reaction medium and conveniently 10° to 30° C. are employed. The reaction time depends on the size of the reactor volume. One hour is typically suitable for the batch sizes tested.

Once the pyrazole derivative of formula III has been formed, reaction of the pyrazole derivative III to close the second ring of the compound and form compound I is accomplished via a reagent which is intended to include any reagent which closes the second ring to form the triazole with the overall loss of water. Again the intermediates may or may not be isolated as desired. A suitable reagent for this step includes any reactive dehydrating agent which does not introduce any undesired side reactions. Typical agents for this purpose are identified in organic chemistry texts such as L. F. Fieser and M. Fieser *Reagents for Organic Synthesis*, John Wiley and Sons, Inc, New York, N.Y. (1968), P 1307. Often these reagents are condensed compounds from which water has already been removed and which are reactive to regain the water. Conveniently, the reagent may be sulfuric acid, ethylene chlorophosphite, phosphorous pentoxide, polyphosphoric acid, dicyclohexylcarbodiimide, phosphorus oxychloride, phosphoryl chloride, phthalic anhydride, or thionyl chloride.

The ring closing step may, for example, be carried out as a simple dehydration step as by heating with sulfuric acid or phosphorus pentoxide or by first halogenating to convert the amide to an imino chloride of formula VI:

with an agent such as phosphorus oxychloride or thionyl chloride and then, in either the same reaction vessel or a separate vessel, heating or adding a base such as triethylamine to displace the halogen and complete the ring closure.

One embodiment consists of reacting acylhydrazino pyrazole derivative II in ethanol for one hour with one equivalent of hydrazine, evaporating the solvent, adding phosphorus oxychloride and refluxing several hours. After pouring on ice, a solvent such as ethyl acetate is added and the organic layer washed with water. Triethylamine is added to make the solution basic and help the reaction to completion, and after one to three hours, the synthesis is completed by washing with water, drying, and evaporating the solvent to yield the pyrazolo[5,1-c]-1,2,4-triazole in good yield.

Alternatively, if $R_3$ is bonded to the acyl carbon through a heteroatom (e.g. in the form of —OR', —NR'R" or —SR' where R' and R" are independently alkyl, aryl, or heterocylic groups), $R_3CO$— can be removed under the appropriate conditions yielding the hydrazino-pyrazole IIIa. This compound is then reacted with an acid chloride, ortho ester, or aldehyde which can be cyclized to a pyrazolo[5,1-c]-1,2,4-triazole by methods such as shown in DD 263060, JP 63-150284, JP 03-220191)

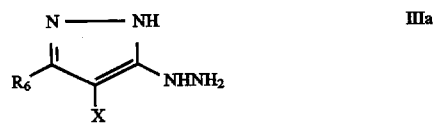

In the structures above $R_3$, $R_6$, and X are as described for III.

In addition to the simplicity of the process, the synthesis of the invention may be accomplished in a short number of industrially safe steps which produce the desired product in high yield and without the production of of photographically undesirable side products such as sulfur.

Unless otherwise specifically stated, substituent groups which may be substituted on molecules herein include any groups, whether substituted or unsubstituted, which do not destroy properties necessary for photographic utility. When the term "group" is applied to the identification of a substituent containing a substitutable hydrogen, it is intended to encompass not only the substituent's unsubstituted form, but also its form further substituted with any group or groups as herein mentioned. Suitably, the group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)

ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)hexanamido, alpha-(4-hydroxy-3-t-butylphenoxy)tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecylphenylcarbonylamino, p-toluylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; carbonyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylaramonium; and silyloxy, such as trimethylsilyloxy.

If desired, the substituents may themselves be further substituted one or more times with the described substituent groups. The particular substituents used my be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

If desired, the photographic element containing a compound of the invention can be used in conjunction with an applied magnetic layer as described in *Research Disclosure*, November 1992, Item 34390 published by Kenneth Mason Publications, Ltd., Dudley Annex, 12a North Street, Emsworth, Hampshire PO10 7DQ, ENGLAND, the contents of which are incorporated herein by reference. When it is desired to employ the inventive materials in a small format film, *Research Disclosure*, June 1994, Item 36230, provides suitable embodiments.

In the following discussion of suitable materials for use with compounds of this invention, reference will be made to *Research Disclosure*, September 1994, Item 36544, available as described above, which will be identified hereafter by the term "Research Disclosure". The contents of the Research Disclosure, including the patents and publications referenced therein, are incorporated herein by reference, and the Sections hereafter referred to are Sections of the Research Disclosure.

Except as provided, the silver halide emulsion containing elements which may be employed with the compounds of this invention can be either negative-working or positive-working as indicated by the type of processing instructions (i.e. color negative, reversal, or direct positive processing) provided with the element. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Scan facilitating is described in Section XIV. Supports, exposure, development systems, and processing methods and agents are described in Sections XV to XX. Desirable photographic elements and processing steps including other components suitable for use in photographic elements of the invention are also described in *Research Disclosure*, Item 37038, February 1995.

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference.

With negative-working silver halide, the processing step described above provides a negative image. The described elements can be processed in the known Kodak C-41 color process as described in The British Journal of Photography Annual of 1988, pages 191–198. Where applicable, the element may be processed in accordance with color print processes such as the RA-4 process of Eastman Kodak Company as described in the British Journal of Photography Annual of 1988, Pp 198–199. Such negative working emulsions are typically sold with instructions to process using a color negative method such as the mentioned C-41 or RA-4 process. To provide a positive (or reversal) image, the color development step can be preceded by development with a non-chromogenic developing agent to develop exposed silver halide, but not form dye, and followed by uniformly fogging the element to render unexposed silver halide developable. Such reversal emulsions are typically sold with instructions to process using a color reversal process such as E-6. Alternatively, a direct positive emulsion can be employed to obtain a positive image.

Preferred color developing agents are p-phenylenediamines such as:

4-amino-N,N-diethylaniline hydrochloride,
  4-amino-3-methyl-N,N-diethylaniline'hydrochloride,
  4-amino-3-methyl-N-ethyl-N-(2-methanesulfonamidoethyl)aniline sesquisulfate hydrate,
  4-amino-3-methyl-N-ethyl-N-(2-hydroxyethyl)aniline sulfate,
  4-amino-3-(2-methanesulfonamido-ethyl)-N,N-diethylaniline hydrochloride and
  4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

The entire contents of copending applications, patents and other publications cited in this specification are incorporated herein by reference.

The preparation of the following intermediates and pyrazolo[5,1-c]-1,2,4-triazoles exemplify the invention.

SYNTHESIS EXAMPLE 1

Preparation of:

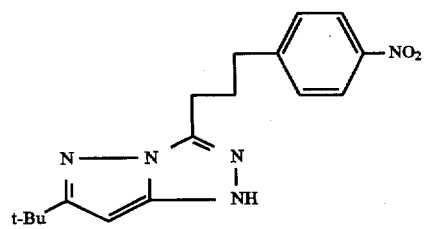

-continued
Scheme

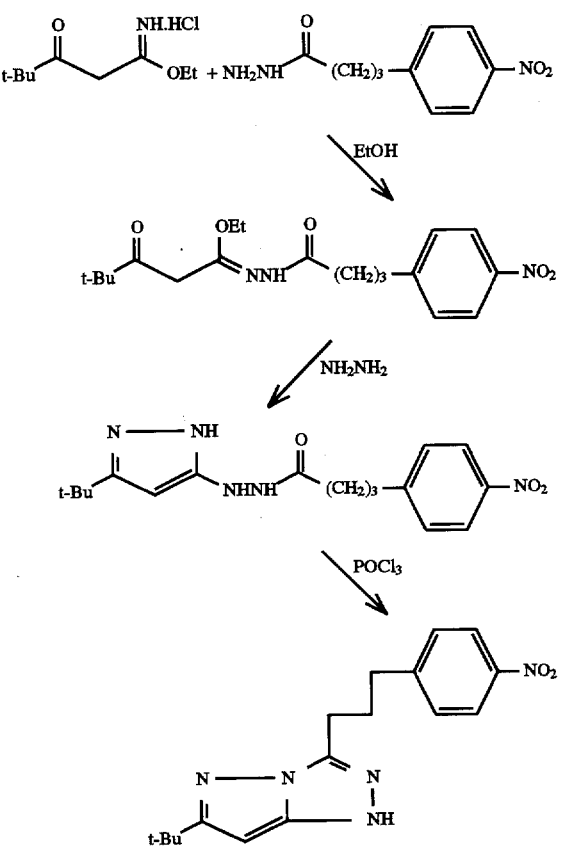

A mixture of 5.0 g (0.024 mol) of the iminoether and 5.5 g (0.024 mol) of the hydrazide were stirred together in 50 ml of ethanol at room temperature for 16 hours. To this suspension was added 0.86 ml (0.027 mol) of hydrazine and stirring was continued for one hour. The mixture was added to water, ethyl acetate added and shaken. The aqueous layer removed and the ethyl acetate layer was washed two times with water, dried over magnesium sulfate, and the solvent evaporated to yield 8.4 g VI as a yellow glass. Without further purification, 1.0 g (0.0029 mol) was refluxed with 3.4 ml (0.037 mol) phosphorus oxychloride for 5 hours, cooled, and added to ice and ethyl acetate. The organic layer was washed with water, 10% sodium carbonate solution, and then water, and 2 ml of triethylamine was added to the undried ethyl acetate layer in the separatory funnel and let sit three hours. Water and dilute hydrochloric acid was then added and the mixture shaken. The aqueous layer was removed and the organic layer washed with water and dried with magnesium sulfate. Evaporation of the organic layer gave a brown oil which was chromatographed on silica gel with ethyl acetate to yield 0.61 g (64%) of pure IV identical with a known sample.

SYNTHESIS EXAMPLE 2

Preparation of:

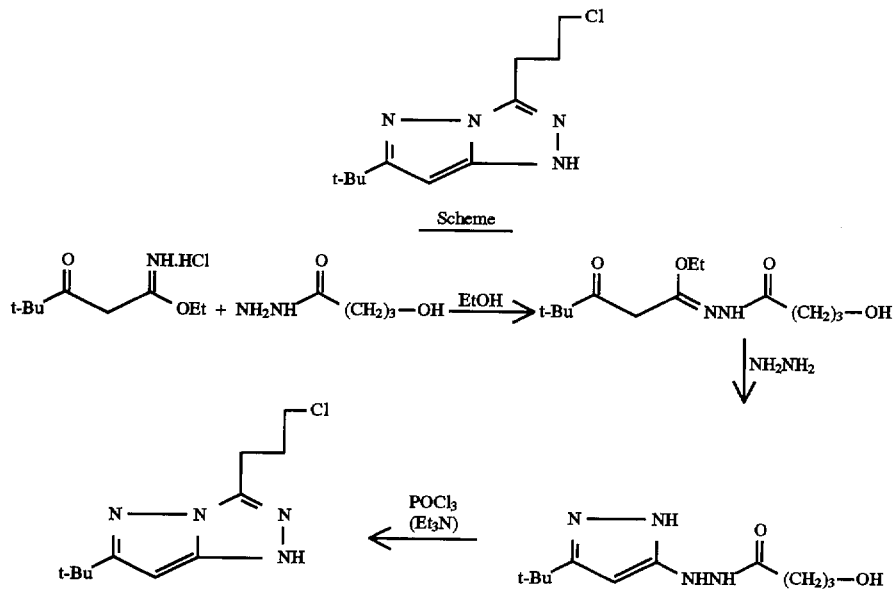

Scheme

A mixture of 1.8 g (0.0085 mol) of the iminoether and 1.0 g (0.0085 mol) of the hydrazide were stirred together in 20 ml of ethanol at room temperature for 2 hours. To this suspension was added 0.30 ml (0.0093 mol) of hydrazine and stirred 12 hours. The mixture was evaporated to an oil. $POCl_3$ (3.5 ml, 0.038 mol) was added and refluxed for three hours. the mixture was cooled, added to ice, ethyl acetate was added and the organic layer washed three times with water and the organic layer made basic (to pH paper) with triethylamine and let sit overnight. The reaction mixture was washed with dilute hydrochloric acid then water and then dried with magnesium sulfate. Evaporation gave a dark gum with was chromatographed on silica gel with 45% ethylacetate in heptane to afford a brown solid, 0.9 gm. Tituration with acetonitrile gave 0.44 gm of the desired product as a white solid.

SYNTHESIS EXAMPLE 3

Preparation of:

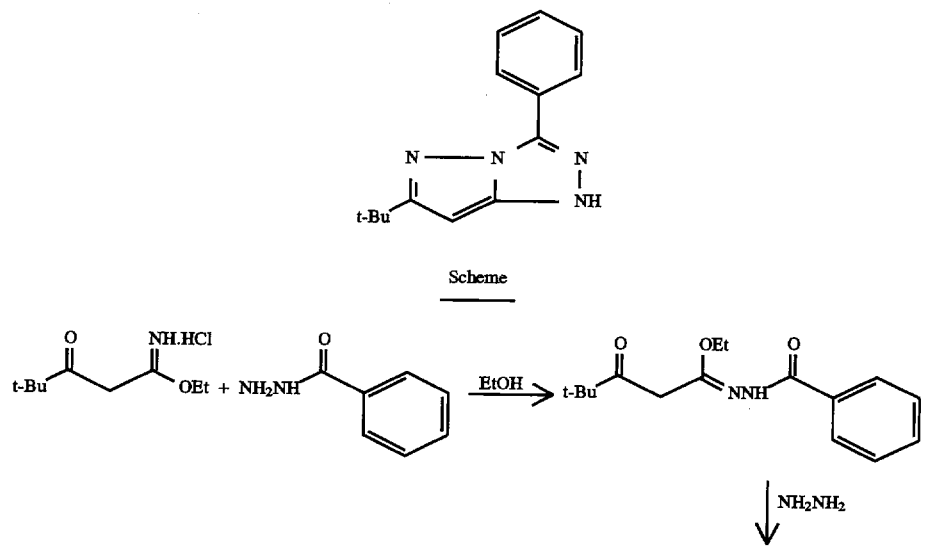

Scheme

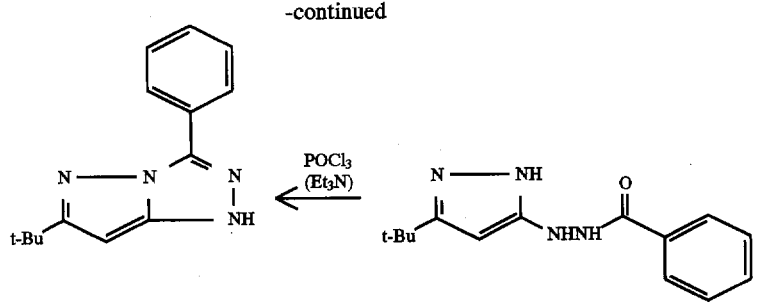

A mixture of 4.58 gm (0.022 mol) of the imino ether and 3.0 gm (0.022 mol) of the hydrazide were stirred in 50 ml ethanol for two hours and the hydrazine (0.77 ml, 0.024 mol) added and the reaction mixture stirred one hour at room temperature. Water and ethyl acetate were added and the organic layer washed three times with water and dried with magnesium sulfate and evaporated to 5.6 gm orange foam. 2.2 ml (0.024 mol) POCl₃ were added and the mixture heated to reflux for five hours. Poured over ice and ethyl acetate added and the organic layer washed three times. The organic layer was made basic with triethylamine and let sit overnight. The ethyl acetate washed with dilute hydrochloric acid, then water, and dried with magnesium sulfate and concentrated. After chromatography with ethyl acetate in heptane (1/3) and tituration with acetonitrile, 3.7 gm of a white solid was obtained.

SYNTHESIS EXAMPLE 4

Preparation of:

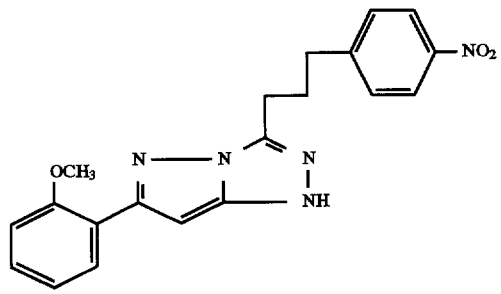

Scheme

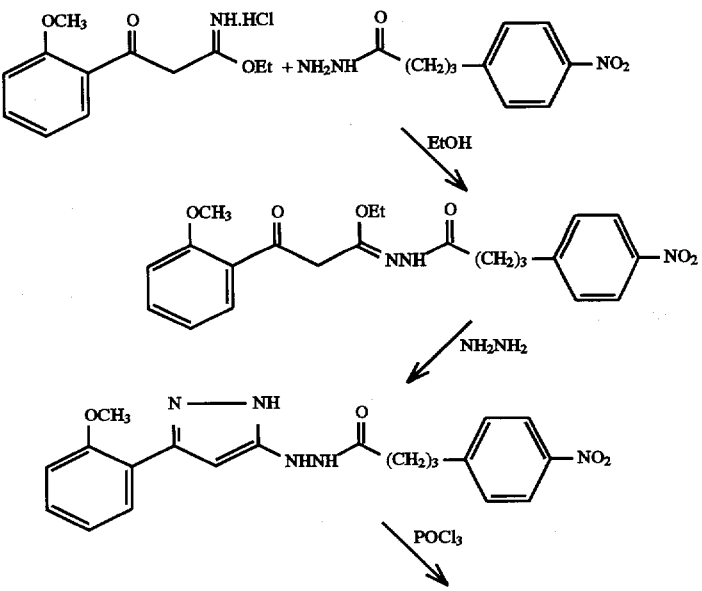

-continued

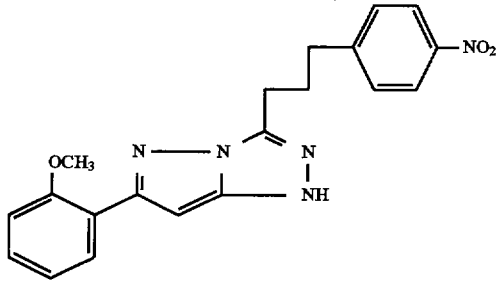

A mixture of 0.86 gm (0.0033 mol) of the imino ether and 0.75 gm (0.0033 mol) of the hydrazide in 5 ml ethanol were stirred at room temperature for two hours. Hydrazine, 0.11 ml (0.0034 mol) was added and the reaction stirred overnight. Water and ethyl acetate were added and the organic layer washed three times with water and dried with magnesium sulfate and evaporated to 1.25 gm of a white foam. This was titurated with ethyl ether to yield 0.70 gm of a white solid. A mixture of 0.50 gm (0.00127 mol) of this solid was refluxed with 1.5 ml (0,0163 mol) of $POCl_3$ for one hour, cooled and poured onto ice. The brown solid was filtered off and stirred in THF with enough $Et_3N$ to make it basic for 3 hours. The mixture was added to ethyl acetate and dilute hydrochloric acid and the organic layer separated and washed three times with water, dried over magnesium sulfate, and dried. After chromatography on silica gel and crystallization from acetonitrile, 0.27 gm of white solid product was obtained.

The entire contents of copending applications, patents and other publications cited in this specification are incorporated herein by reference.

What is claimed is:

1. A process for making a compound of formula III

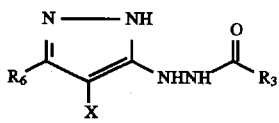

wherein $R_6$ is a group bonded to the rest of the molecule by a carbon atom;

$R_3$ is a group containing a carbon atom and bonded to the rest of the molecule by a carbon atom or by a heteroatom; and X is hydrogen or a substituent, comprising:

reacting with hydrazine a compound of formula II

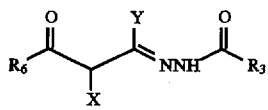

wherein $R_3$, $R_6$, and X have the same meaning as for formula III, and Y is a nucleofugal leaving group selected from halide, alkoxide, and phenoxide.

2. The process of claim 1, wherein:

$R_6$ is a group bonded to the rest of the molecule by a carbon atom;

$R_3$ is a group containing a carbon atom and bonded to the rest of the molecule by a carbon atom or by a heteroatom; and X is selected from the group consisting of
 (1) hydrogen and
 (2) a group which is either
  (a) capable of being eliminated during reaction with an oxidized photographic developer, or
  (b) a group capable of being eliminated or replaced by a group as described for (a) during a reaction subsequent to reaction with the oxidized developer.

3. The process of claim 1 wherein $R_6$ comprises a methyl group or a tertiary alkyl group.

4. The process of claim 1 wherein $R_3$ is a substituted alkyl group.

5. The process of claim 4 wherein $R_3$ is an aminoalkyl group.

6. The process of claim 1 wherein the reaction is conducted in an inert organic solvent.

7. The process of claim 6 wherein the solvent is selected from the group consisting of alcohols, methylene chloride, chloroform, tetrahydrofuran, diethyl ether, ethyl acetate, acetic acid, pyridine, and acetonitrile.

8. The process of claim 7 wherein the solvent is selected from the group consisting of methanol, ethanol and ethyl acetate.

9. The process of claim 1, wherein X is a substituent.

* * * * *